(12) United States Patent
Mizus

(10) Patent No.: US 9,138,253 B2
(45) Date of Patent: *Sep. 22, 2015

(54) SYSTEM FOR ACCESS INTO BODILY CAVITY

(71) Applicant: Irving Mizus, Chevy Chase, MD (US)

(72) Inventor: Irving Mizus, Chevy Chase, MD (US)

(*) Notice: Subject to any disclaimer, the term of this patent is extended or adjusted under 35 U.S.C. 154(b) by 33 days.

This patent is subject to a terminal disclaimer.

(21) Appl. No.: 14/187,722

(22) Filed: Feb. 24, 2014

(65) Prior Publication Data

US 2014/0171906 A1 Jun. 19, 2014

Related U.S. Application Data

(62) Division of application No. 13/346,346, filed on Jan. 9, 2012, now Pat. No. 8,801,669, which is a division of application No. 11/067,729, filed on Mar. 1, 2005, now Pat. No. 8,105,284.

(51) Int. Cl.
| | |
|---|---|
| *A61B 17/34* | (2006.01) |
| *A61M 25/00* | (2006.01) |
| *A61M 1/00* | (2006.01) |
| *A61M 25/06* | (2006.01) |
| *A61M 5/158* | (2006.01) |

(52) U.S. Cl.
CPC ......... *A61B 17/3417* (2013.01); *A61B 17/3498* (2013.01); *A61M 1/0023* (2013.01); *A61M 25/0021* (2013.01); *A61B 17/3415* (2013.01); *A61M 5/158* (2013.01); *A61M 25/065* (2013.01)

(58) Field of Classification Search
CPC .......... A61B 17/3415; A61B 17/3417; A61B 17/3498; A61M 1/0023; A61M 5/158; A61M 25/0021; A61M 25/0023; A61M 25/065
See application file for complete search history.

(56) References Cited

U.S. PATENT DOCUMENTS

| | | | | |
|---|---|---|---|---|
| 2,421,959 | A * | 6/1947 | Norris | 604/183 |
| 3,559,643 | A * | 2/1971 | Pannier et al. | 604/171 |
| 4,051,852 | A * | 10/1977 | Villari | 604/183 |
| 4,471,778 | A * | 9/1984 | Toye | 128/207.29 |
| 4,581,019 | A * | 4/1986 | Curelaru et al. | 604/164.05 |
| 4,619,644 | A * | 10/1986 | Scott | 604/506 |
| 4,838,866 | A * | 6/1989 | Marshall, Sr. | 604/152 |
| 5,254,092 | A * | 10/1993 | Polyak | 604/99.02 |
| 5,304,147 | A * | 4/1994 | Johnson et al. | 604/183 |
| 6,004,293 | A * | 12/1999 | Bell | 604/160 |
| 6,475,193 | B1 * | 11/2002 | Park | 604/191 |
| 7,581,559 | B2 * | 9/2009 | Bausmith, III | 137/512 |
| 8,105,284 | B2 * | 1/2012 | Mizus | 604/160 |
| 8,801,669 | B2 * | 8/2014 | Mizus | 604/160 |
| 2002/0007157 | A1 * | 1/2002 | Azzolini | 604/247 |
| 2004/0010282 | A1 * | 1/2004 | Kusleika | 606/200 |
| 2004/0087964 | A1 * | 5/2004 | Diaz et al. | 606/108 |

* cited by examiner

*Primary Examiner* — Andrew Gilbert
(74) *Attorney, Agent, or Firm* — Sughrue Mion, PLLC

(57) ABSTRACT

An assembly and method for percutaneous placement of a catheter comprising an elongated hollow catheter having a distal end and a reduced cross-section portion at a proximal end thereof. An introducer needle is slidably mounted over said catheter. The introducer needle has an elongated slit adapted to slide over the reduced cross-section portion to separate the needle from the catheter. A syringe may be attached to the proximal end of the catheter. Also, a valve may be attached to the catheter to permit easy collection of fluid.

6 Claims, 4 Drawing Sheets

SYSTEM FOR ACCESS INTO BODILY CAVITY

CROSS REFERENCE TO RELATED APPLICATIONS

This application is a divisional of allowed U.S. application Ser. No. 13/346,346, filed Jan. 9, 2012, which is a divisional of U.S. application Ser. No. 11/067,729, filed Mar. 1, 2005, now U.S. Pat. No. 8,105,284, the entire disclosures of which, including the drawings, are incorporated herein by reference in their entirety.

BACKGROUND OF THE INVENTION

1. Field of the Invention

This invention relates to medical instruments and in particular a system that establishes percutaneous access to a blood vessel or body cavity (which would include an abscess or pleural or peritoneal or pericardial or epidural or subarachnoid spaces).

2. Related Art

It is frequently necessary to establish access to an internal portion of the body for the purpose of removal of fluid, administration of medication, establishing a drainage path and the like. A typical application is placement of a catheter in a blood vessel for collection of blood over an extended period of time. This same catheter can be used for the intravenous administration of drugs and anesthesia. Delivery is not limited to vascular access but also for establishing caudal and lumber epidural blocks for the production of local or regional anesthesia by infiltration techniques. Another common use for catheter placement is to establish a drainage path for the pleural or peritoneal or pericardial spaces or from a surgery site or abscess.

As used herein, the term "proximal end" refers to that portion of the system that is above the skin line and is accessible. The term "distal end" refers to that portion of the system that is inserted into the body, such as the tip of the needle or end of the catheter.

A typical procedure involves the placement of a catheter, typically flexible and of a plastic material, into the space occupied area with the proximal end affixed at skin level. A thorocentesis kit may be used which employs a needle with a catheter mounted concentrically on the outside. The length of the needle is somewhat longer that the catheter so that the sharp tapered end projects beyond the end of the catheter. The outer end of the catheter is tapered to provide a smooth transition from the outer diameter of the needle to that of the catheter. The inner end of the catheter is sleeved with a connector for subsequent connection to a collection bag, syringe or cut-off valve. A syringe is attached to the end of the needle. The catheter is then free to slide on the outside of the needle but is prevented from coming off the needle at the proximal end by the attachment connector of the needle to the syringe.

In this procedure the needle pierces the skin and any underlying tissue carrying with it the catheter. Since the proximal end of the catheter is stopped by the syringe attachment, it advances at the same rate as the needle. Once a sufficient depth of penetration is achieved by the needle, the clinician simultaneously withdraws the needle while advancing the catheter. The needle acts as a guide for the catheter. Generally accumulation of a small amount of fluid in the syringe provides an indication that the needle has penetrated to the destination location. The catheter is advanced until its distal end is at the desired location and then the needle is totally withdrawn. The proximal end of catheter may then be attached to a collection bag for drainage or collection of bodily fluid. It may also be used as a port for the delivery of medicine by subsequent introduction of a needle with a syringe loaded with a drug. The catheter proximal end can also be fitted with a valve for capping the catheter.

One disadvantage of this technique is that the fact that the catheter-flow circuit must be broken in order to remove the introducer needle as the needle is removed the catheter is in open fluid communication with the environment so that air can enter into the cavity if the pressure gradient favors retrograde flow. Another disadvantage of this technique includes the possibility of an unintended needle stick of the clinician upon his or her withdrawal of the needle because of the technique and materials used in the above described system. Yet another disadvantage of this prior art technique is that the needle must be as long as the catheter making it cumbersome to handle and manipulate.

Another technique in use employs a large diameter needle that is used to establish access to the body location where the catheter will be placed. A wire is then passed inside the needle until it has reached the approximate location at or beyond the distal end of the needle. The needle is then withdrawn and the wire remains. A catheter is then slid over the wire as the wire is removed and the catheter remains behind. A problem with this technique involves the number of steps required each of which individually and collectively add levels of potential complications and/or inaccurate distal catheter placement. Frequently, the distal end of the catheter will abut or sometimes dig into the wall of the vessel preventing the withdrawal or delivery of fluid.

SUMMARY OF INVENTION

Given the disadvantages of the prior art, an object of this invention is to provide a system providing reliable access and placement of a catheter into a bodily cavity, an organ, or blood vessel.

Another object of this invention is to provide a medical procedure involving a method of catheter placement that is reliable and safer than prior art allows which includes a system that maintains a closed circuit from the beginning to the end of the procedure.

Yet another object of this invention is to provide a percutaneous kit for intra-vascular or intra-cavitary catheter placement for the administration of drugs and/or evacuation of fluid.

These and other objects of this invention are accomplished by means of a needle/catheter combination with a beveled introducer needle able to slide over the catheter. The catheter is longer than the needle. The outer diameter of the catheter is substantially equal to the internal diameter of the needle to permit sliding movement over the catheter. The introducer needle has a longitudinal slit running its entire length and a flange at the distal end with a knurled grip. The slit defines an open groove running the length of the needle.

The catheter has a connector section at the proximal end for attachment of a syringe or valve. The connector has a section of reduced size in a grooved shape whose thickness is equal to the width of the longitudinal slit in the introducer needle. This groove will therefore permit the needle to pass over it. In one embodiment the connector section is oriented at an angle to the catheter and the reduced section is on the connector portion and oriented in alignment with the groove which enables the needle to align with the groove in a seamless manner. In another embodiment, the connector is positioned axially at the proximal end of the catheter and the section of reduced size is an elongated region of reduced cross-sectional size above the connector.

Another aspect of this invention is the provision of a single directional dual ball suction/delivery valve for the collection of fluid. The valve has three ports, an output port with a valve attached to the catheter, an input valve port coupled to a collection bag and a port in fluid communication with both valves connected to a source of reduced pressure such as a syringe. When suction is created by the syringe the valve ball moves toward a limiting post opening the orifice emptying the proximal catheter lumen while simultaneously causing a second ball to seal the orifice of the catheter conducting material to a collection receptacle. When positive pressure is applied by the syringe the first ball is caused to seal closed the orifice to the proximal end of the introduced catheter and simultaneously causing the second ball to move away from the orifice to the catheter communicating material to the collection receptacle with the ball being stopped by a limiting post.

In operation of the system, the clinician holds the introducer needle by one hand and stabilizes the catheter with the other hand. The catheter is positioned inside the needle and slightly behind the beveled distal end. The needle punctures the skin and underlying tissue to a desired depth of penetration. The catheter is then advanced and the needle withdrawn by sliding the needle over the catheter as the catheter is advanced. When the proximal end of the needle, with the flange, reaches the connector section (or area of reduced cross-section) it is stripped off the catheter along the longitudinal groove. As an alternative to complete removal of the needle, it can be docked on the catheter for later removal but the danger in the delay of removal is that it potentially exposes an individual to the contents of the space entered and adds the risk for catheter puncture or shearing by the introducer needle tip (if mishandled). A syringe and/or a valve are attached to the connector before the procedure begins.

These and other aspects of this invention will become apparent from the drawings and the description of the preferred embodiments that follow.

DESCRIPTION OF THE PREFERRED EMBODIMENTS

Figure 1:
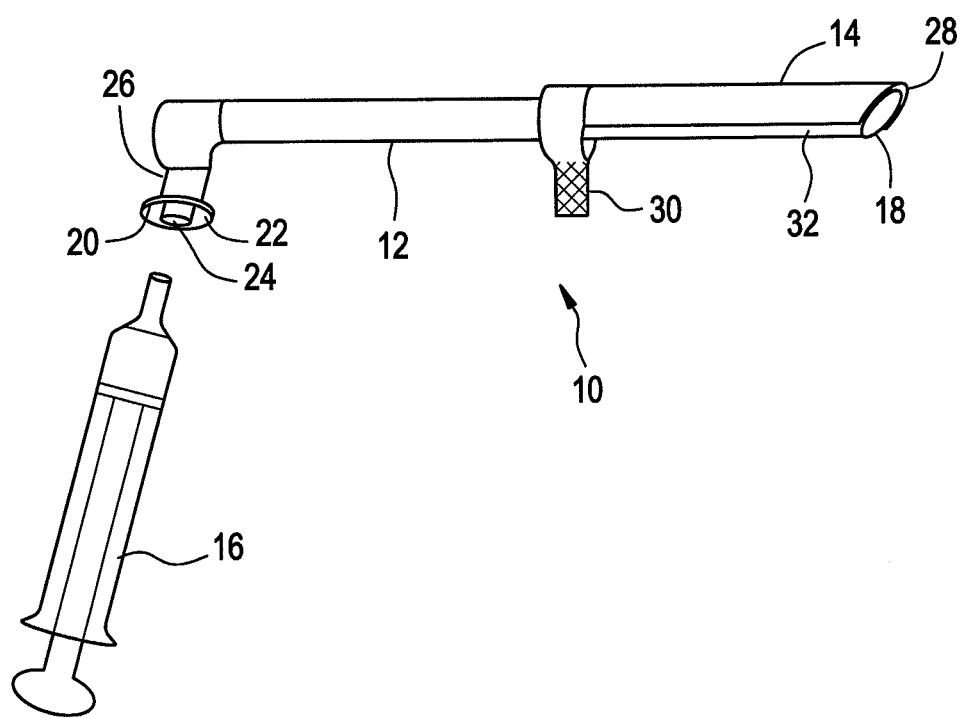
FIG. 1 is a perspective view of a first preferred embodiment of this invention illustrating the components thereof.

Referring to FIG. 1 a schematic perspective view illustrates the essential components of this invention. The kit 10 comprises three components, a catheter 12, an introducer needle 14 and a syringe body 16. The syringe 16 is conventional and need not be discussed further.

The catheter 12 is typically an elongated hollow plastic tube of suitable internal diameter and stiffness. The distal end 18 is beveled and tapered to aid in penetration. The bevel matches that of the needle. The proximal end has a connector section 20. In this preferred embodiment the connector section 20 is oriented 90° to the axis of the catheter via an elbow portion. It is apparent that the connector section 20 need not be at right angles to the axis of the connector. This section has a flange 22 and a hole 24 into which the syringe 16 is inserted. It is apparent that a valved "Y" connector can also be attached at this point instead of the syringe.

The connector has a flattened section 26 which is aligned with the longitudinal axis of the catheter that is parallel to the internal bore of the catheter. The outer thickness of the section 26 matches the width of the slit of the introducer needle, as will be explained herein.

The introducer needle 14 is metal or rigid plastic. It has a distal end that is sharpened and beveled. The proximal end has a holding flange 30. This is in the form of a tab portion suitably roughened by knurling or the like to provide a secure thumb and finger grip. Preferably the tab portion is wrapped around the needle to provide two protruding ends.

The introducer needle has a longitudinal groove or slit running the length of the needle. As illustrated the needle circumference is about 270° with the groove comprising about 90°. The exact angular extent of the wrap around of the needle 14 vis-à-vis the catheter 12 is not critical so long as the needle is held in position on the catheter, that is, a co-axial relationship is maintained during the placement phase of the procedure. The groove may be as large as slightly less than 180° in the case of a relatively stiff and/or large diameter catheter where in either case the catheter will support the needle. It may alternatively be relatively thin in the case of flexible catheter requiring a greater degree of support about its circumference.

Figure 2:
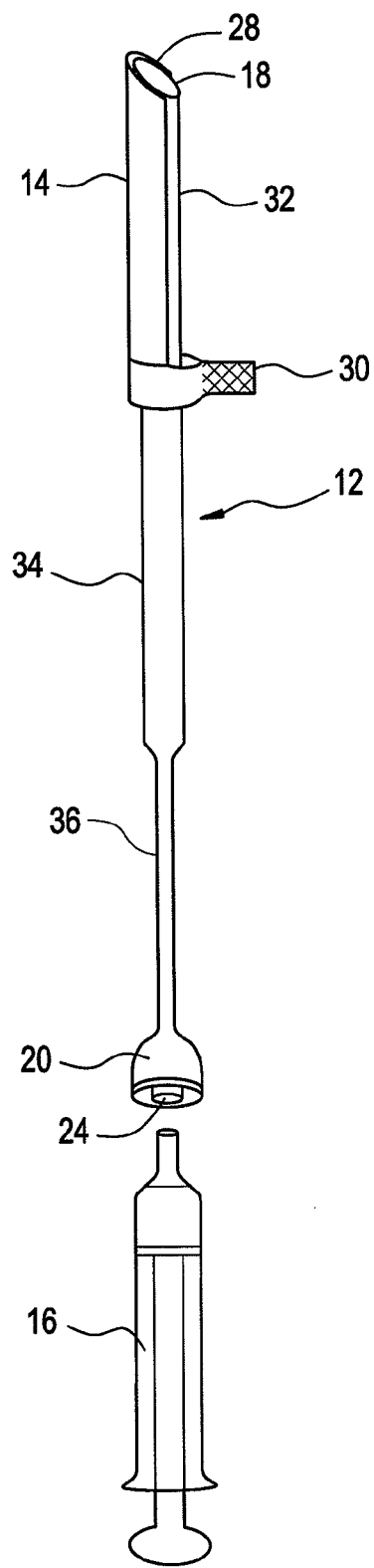
FIG. 2 is a perspective view of a second preferred embodiment of this invention illustrating the components thereof.

A second preferred embodiment is illustrated in FIG. 2 Like elements are identified with the same numbering as in FIG. 1 and need not be discussed. In this embodiment, the catheter 12 has two sections, a full diameter portion 34 and a reduced diameter portion 36. The introducer needle 14 is mounted on the full diameter portion 34 and is slidable as in the first preferred embodiment. The reduced diameter portion 36 is used to remove the needle from the catheter, as will be described herein. While the connector is illustrated as coaxial with the catheter, it is apparent that it could be angled as in the first preferred embodiment.

The operation of the invention will now be described. In the FIG. 1 embodiment the catheter 12 and the introducer needle 14 are either pre-assembled as illustrated in the figure or the needle is slid over the distal end of the catheter. The distal ends of the needle and catheter are aligned so that the bevels 18 and 28 co-incident with each other. The clinician then holds the catheter in one hand by the knurled portions of the needle flanges and the tab 30 with the other. The assembled needle 14 and catheter 12 are then percutaneously inserted intra-vascular or intra-cavitary to a proximal position. Then, holding the needle in a stationary position, the catheter is advanced to the desired placement position. As such, the needle moves relatively backward toward the proximal end that is closer to the connector 20.

Figure 4:
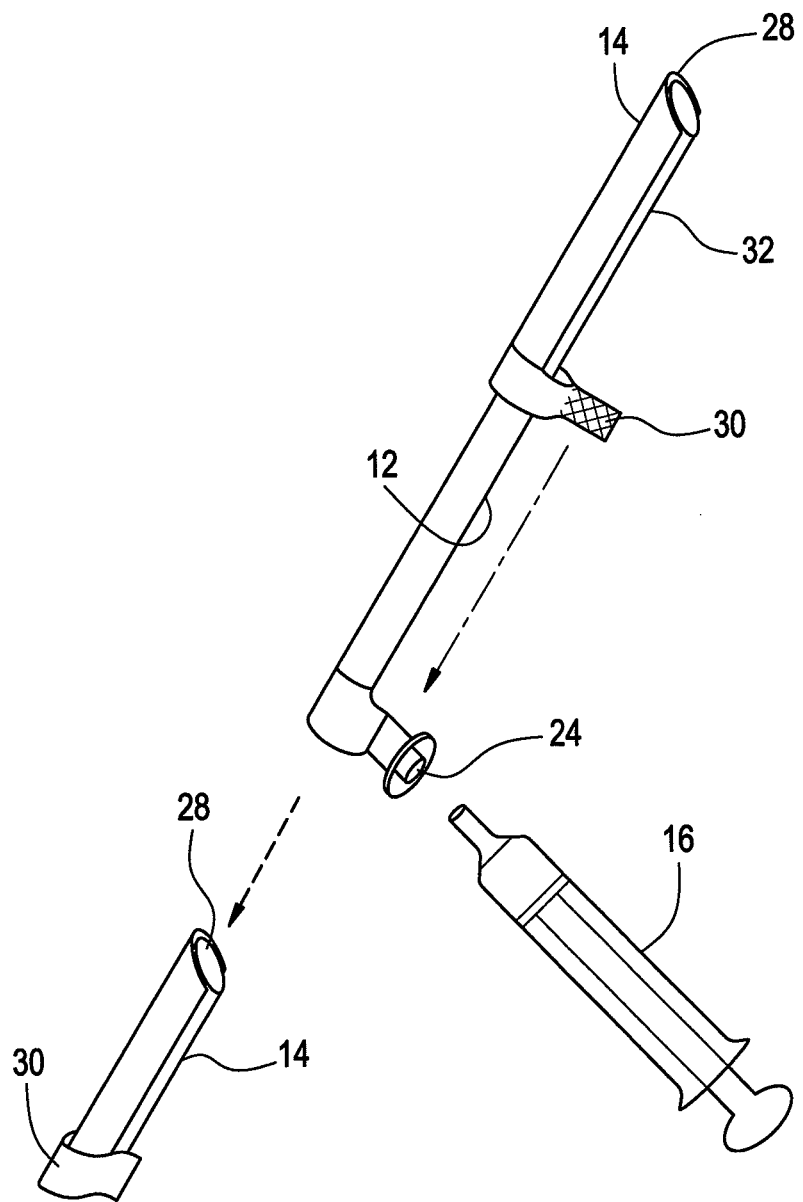
FIG. 4 is a schematic view illustrating the method of use of this invention.

With the catheter in its proper position, the needle is fully retracted by a sliding movement using the tab 30. When the tab reaches the connector 22, the tab portions 30 are either spread apart or peeled back to a position opposite the slit 32. The needle then passes over the connector with the slit riding over the reduced cross-sectional portion 26. As such the needle is removed and can be discarded by merely holding it and moving the needle with the tabs 30. This is illustrated in FIG. 4. Alternatively, the needle 14 may be "docked", that is left in position adjacent the connector for removal at a later date.

In the case of the embodiment of FIG. 2, the introducer needle 14 is slid down the length of the catheter until it reaches the reduced diameter portion 36. The tabs are then reversed and the needle stripped off the catheter. As in the FIG. 1 embodiment, the needle may be docked over the reduced section but again the risks related to delayed needle removal include catheter puncture or shearing by the introducer needle tip if mishandled.

In both embodiments the syringe 16 or a stop valve, not illustrated, can be attached to the catheter at any point in the procedure. That is, it may be affixed to the connector 20 before the needle is introduced or after the needle is stripped off, or at any time in between. The syringe can be used for the introduction of medicine or as a space occupied evacuation system.

It will be appreciated that by this combination of introducer needle and catheter achieves accurate percutaneous placement of a catheter and yet the needle can be easily withdrawn and safely removed without disturbing the catheter or forcing a break in the collection circuit.

Figure 3:
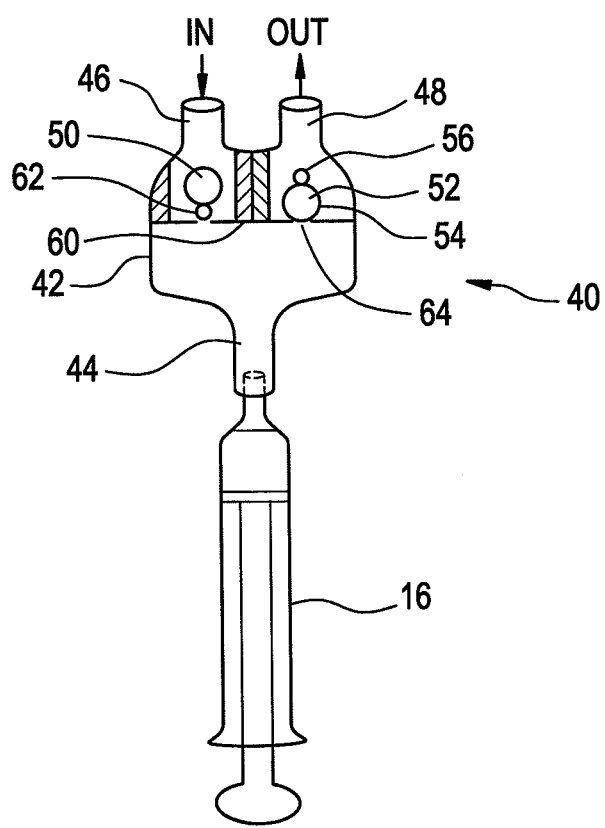
FIG. 3 is a schematic view of the valve used in accordance with this invention.

A valve for use with this system is illustrated in FIG. 3. The valve 40 has a hollow body portion 42 with three ports 44, 46 and 48. The body portion 42 has an internal wall 60 with a pair of thru-holes 62, 64. Port 44 is an open conduit to be attached to a source of reduced pressure such as suction or, as illustrated, syringe 16. Two stop elements 50, 52 are positioned in ports 46 and 48 respectively. The stop elements each have a stopper 54 and a guide 56. The stoppers 54 are sized to seal either the port 46 and prevent backflow into port 46 or opening 64. The stop elements are reversed, as shown, so that port 46 constitutes and "IN" and port 48 an "OUT".

The port 46 is typically connected to the catheter 12 via the connector 20. The port 48 is attached to a collection bag, not illustrated. In operation with these components attached, when the syringe piston is withdrawn pressure within the body 42 is reduced causing stopper elements 50 and 52 to move toward and seat on the wall 60. In this position, fluid communication is established between catheter 12 and hollow body portion 42 while the stopper 54 seals the OUTPUT 48. By the application of further suction by action of the syringe, the body 42 and potentially the syringe body 16 will fill with fluid. When the piston is advanced, the stoppers 50 and 52 move toward the ports 46 and 48. This seals the INPUT 46 and opens the OUTPUT 48 allowing the fluid to be collected in the collection bag.

It will be appreciated that if the source of suction coupled to port 44 is another source, such as a continuous vacuum, the material collected can be immediately and directly removed.

It is apparent that alternatives of these embodiments are within the scope of this invention. For example, the cross section of the needle and catheter need not be round. It can be configured to any cross-sectional shape desired as a function of the procedure, such as oval, triangular or the like. The tab on the introducer needle does not have to be knurled to provide a grip. It may be perforated, corrugated, roughened by other techniques or made sticky to tactile grip. The tab may be modified to be a fixed protrusion on the needle at a position that does not block the groove.

The dimensions of the longitudinal groove and the geometry are functions of the materials used and the diameter of the catheter. In the case of a relatively thin and/or flexible catheter the groove may be thin and still allow the needle to be stripped off. If the catheter is relatively stiff, the groove may be larger, approaching one-half the circumference of the needle yet the needle will still be held on the catheter but easily stripped off. Although not illustrated, the groove may have a wider circumferential portion at the proximal end to facilitate the stripping process by "starting" the needle off of the catheter.

Additionally the connector section can have a stop valve attached or made integral to it to prevent fluid communication between the catheter and ambient conditions.

I claim:

1. A method of removing fluid from a body cavity by the percutaneous placing a catheter having an elongated hollow catheter with a reduced cross-section portion at a proximal end thereof and, an introducer needle slidably mounted over said catheter, said introducer needle having an elongated slit comprising the steps of; advancing said needle and said catheter percutaneously to a desired position, withdrawing said needle while maintaining the position of said catheter and, sliding said elongated slit over said reduced cross-section portion to separate said introducer needle from said catheter, attaching a valve assembly having three ports to the proximal end of said catheter using one of said three ports, attaching source of reduced pressure to a second port, attaching a collection device to said third port, operating said source of reduced pressure to draw fluid from said catheter and into said collection device by operation of said valve assembly.

2. The method of claim 1 wherein the step of attaching a source of reduced pressure comprises the step of attaching a syringe to the proximal end of said catheter.

3. The method of claim 2 wherein the step operating said source of reduced pressure comprises the step of pleural evacuation by withdrawal of bodily fluid through said catheter and into said syringe.

4. The method of claim 1 further comprising the step of introducing a drug intra-vascularly from said syringe and into said catheter.

5. The method of claim 1 further comprising the step of introducing a drug intra-cavitarly from said syringe and into said catheter.

6. The method of claim 1 wherein the step of withdrawing said needle comprises a step of temporarily docking said needle prior to complete withdrawal.

* * * * *